United States Patent
Gow et al.

(10) Patent No.: US 7,381,434 B2
(45) Date of Patent: *Jun. 3, 2008

(54) **METHODS AND COMPOSITIONS OF *ARECA CATECHU***

(75) Inventors: Robert T. Gow, Naples, FL (US); Brian Pierce, Thousand Oaks, CA (US); John Pierce, Thousand Oaks, CA (US); William Birdsall, Naples, FL (US)

(73) Assignee: HerbalScience LLC, Naples, FL (US)

( * ) Notice: Subject to any disclaimer, the term of this patent is extended or adjusted under 35 U.S.C. 154(b) by 389 days.

This patent is subject to a terminal disclaimer.

(21) Appl. No.: 10/818,439

(22) Filed: Apr. 5, 2004
(Under 37 CFR 1.47)

(65) Prior Publication Data

US 2004/0202738 A1   Oct. 14, 2004

Related U.S. Application Data

(63) Continuation-in-part of application No. 10/408,896, filed on Apr. 8, 2003, now abandoned, and a continuation-in-part of application No. 10/408,888, filed on Apr. 8, 2003, now abandoned.

(51) Int. Cl.
*A61K 36/88* (2006.01)
*A61K 36/00* (2006.01)
*A61K 31/44* (2006.01)

(52) U.S. Cl. .................. 424/727; 424/776; 424/725; 514/356

(58) Field of Classification Search .............. None
See application file for complete search history.

(56) References Cited

U.S. PATENT DOCUMENTS

| | | | | |
|---|---|---|---|---|
| 1,447,400 | A | * | 3/1923 | Stoll ........................... 546/39 |
| 4,064,253 | A | * | 12/1977 | Khoe ........................ 514/356 |
| 4,710,508 | A | * | 12/1987 | Bergmeier et al. .......... 514/357 |
| 6,352,713 | B1 | * | 3/2002 | Kirschner et al. .......... 424/441 |
| 6,414,036 | B1 | * | 7/2002 | Ninkov ....................... 514/731 |
| 7,037,524 | B2 | * | 5/2006 | Gow et al. ................... 424/470 |
| 2003/0144639 | A1 | * | 7/2003 | Gehling ...................... 604/360 |
| 2005/0053678 | A1 | * | 3/2005 | Gow et al. ................... 424/734 |

FOREIGN PATENT DOCUMENTS

| | | | |
|---|---|---|---|
| CA | 1133831 | * | 10/1982 |
| CN | 1120941 | * | 4/1996 |
| JP | 09286734 | * | 11/1997 |
| KR | 2002074905 | * | 10/2002 |

OTHER PUBLICATIONS

Su, S. G. et al., Extraction of betal quid with supercritical carbon dioxide, Journal of the Chinese Chemical Society (Taipei Taiwan), 1993, pp. 517-522, vol. 40, No. 6.
Kumosani, T.A. et al., Effect of *Areca* nut extracts on some organ markers from rat serum in vivo, Journal of King Saud University Science, 2003, pp. 1-10, vol. 15, No. 1.
Database WPI, Section Ch, Week 198714, Derwent Publications Ltd., London, GB; AN 1987-099102, XP002292553 & JP 62 048677 A (Nippon Shinyaku Co. Ltd.), Mar. 3, 198.
Database WPI, Section Ch, Week 199517, Derwent Publications Ltd., London, GB; AN 1995-125567, XP002292554 & JP 07 047108 A (Nippon Seifun KK), Feb. 21, 1995.
Database WPI, Section Ch, Week 199939, Derwent Publications Ltd., London, GB; AN 1999-461446, XP002292555 & JP 11 192069 A (Sawaguchi K), Jul. 21, 1999.
Sundqvist, K. et al., Cytotoxic and genotoxic effects of *Areca* nut-related compounds in cultured human buccal epithelial cells, Cancer Research, 1989, pp. 5294-5298, vol. 49, No. 19.
Wenke, G. et al., Betel quid carcinogenesis 1. In vitro N-nitrosation of arecoline, Carcinogenesis (Oxford), 1983, pp. 169-172, vol. 4, No. 2.
Jeng, J.H. et al., Role of *Areca* nut in betal quid-associated chemical carcinogenis: current awareness and future perspectives, Oral Oncology (Elsevier Science, Oxford), 2001, pp. 477-492, vol. 37, No. 6.

* cited by examiner

*Primary Examiner*—Christopher R. Tate
(74) *Attorney, Agent, or Firm*—Troutman Sanders LLP

(57) ABSTRACT

This invention comprises methods and compositions of *Areca catechu*. Methods of the present invention comprise extracting plant material of *Areca catechu* so that compositions having characteristics different from those of native plant materials are obtained. Compositions comprising food aids and other dietary supplements are also taught.

9 Claims, No Drawings

METHODS AND COMPOSITIONS OF *ARECA CATECHU*

RELATED APPLICATIONS

This application is a continuation-in-part of U.S. patent application Ser. No. 10/408,888, filed Apr. 8, 2003, now abandoned, and is a continuation-in-part of U.S. patent application Ser. No. 10/408,896, filed Apr. 8, 2003, now abandoned, both of which are incorporated by reference in their entireties as if specifically set forth herein.

FIELD OF THE INVENTION

The present invention is related to *Areca catechu* products, compositions and methods for making and using the same. More specifically, the present invention is related to methods for making *Areca catechu* compositions with characteristics differing from native plant material.

BACKGROUND OF THE INVENTION

Areca, a type of palm tree also known as *Areca catechu*, is generally cultivated in India, Southeast Asia, the East Indies and East Africa. The fruit of the Areca tree is a nut containing a single seed having a thin seed coat. The nut of the *Areca catechu* tree contains several pyridine-derived alkaloids, including arecoline, Arecaidine, guvacoline and guvacine which may be as high as 1.7% of the nut's make-up. In nature, the highest single alkaloid component concentration in Areca nut is the arecoline, a methyl ester. (1)

The Areca nut is known around the world for its stimulating effects, and it is chewed by millions of people who seek the stimulating properties of the nut. Betel quid is the combination of *Areca catechu* nut and piper betel leaf, and other components, and is the most common use of the Areca plant. There are approximately 600 million betel quid chewers in the world. Betel quid chewing is a major etiologic factor of oral cancer. It has been found that Areca nut and arecoline inhibit the growth of oral mucosal fibroblasts and keratinocytes. The effects of long-term use include oral submucosus fibrosis, leukoplakia and oral cancer. Studies have shown that Areca nut extract induces DNA breaks and unscheduled DNA synthesis and differentiation of oral keratinocytes. Arecoline also displays genotoxic effects.

The autonomic effects of Areca on the user include sweating and facial flush; skin temperature rises and heart rate also increases while chewing Areca. Specifically, the alkaloids arecoline and Arecaidine, although initially causing a brief depressor response, subsequently produce an increase in arterial blood pressure and heart rate. These stimuli are mediated through muscarinic $M_1$ receptors.

In animals, arecoline, Arecaidine, guvacoline and guvacine are known to possess activity as agonists at muscarinic acetylcholine receptors. Additionally, arecoline has been shown to have indirect effects on catecholamine levels, while Arecaidine and guvacine inhibit gamma-aminobutyric acid (GABA) receptor uptake in micromolar concentrations.

The chewing of betel quid has led to increased levels of oral cancers. For example, in the United Kingdom, with its large population of Southeastern Asians, many of whom routinely chew betel quid, there are over 3800 new cases of oral cancer and 1700 deaths each year. One combination of betel quid uses the betel pepper leaf as a wrapper for various fillings that include Areca palm nut, as pastes, crushed fragments or shavings, along with tobacco, saffron, slaked lime, and aromatic spices and seeds. Some of these combinations add to the carcinogenicity of betel quid. The presence of arecoline, which is the major alkaloid compound in the Areca nut, has been linked to precancerous conditions, including oral mucosal fibrosis.

What is needed are compositions that provide the desired physiological effects provided by *Areca catechu* nut and that have lowered carcinogens, particularly arecoline. What is also needed are methods of altering the alkaloid profile of extracts of the Areca nut to provide compositions having alkaloid profiles that are different from the native plant material.

SUMMARY OF THE INVENTION

The present invention comprises methods and compositions of *Areca catechu*. Methods of the invention comprise methods of extraction of compounds from plant source material of *Areca catechu*, methods of making pharmaceutical or nutriceutical products comprising *Areca catechu*, and methods of use of the extracted products and pharmaceutical and nutriceutical products. Compositions of the present invention comprise compounds isolated from the plant material of *Areca catechu*. An aspect of compositions of the present invention comprise extraction products of *Areca catechu* comprising alkaloid profiles that are not found in the natural plant material or products made prior to the present invention. A specific alkaloid profile comprises a ratio of Arecaidine to arecoline wherein the ratio of Arecaidine to arecoline, by weight, is greater than about 1.0. Other compositions comprise alkaloid profiles wherein the amount of Arecaidine and guvacine, either individually or in combination, in the extracted product is greater than the amount of arecoline and guvacoline, either individually or in combination.

One embodiment of the present invention comprises methods for extracting alkaloids from the Areca seed. Methods comprising use of supercritical $CO_2$ extraction methods are used to isolate one or more alkaloids from the seed in the form of a paste, oil, and/or resin. Methods of the present invention comprise extraction of the nut by grinding the nut and drying it, extracting the ground nut powder with one or more solvents, including but not limited to, water, alcohol, water and alcohol solutions, carbon dioxide, fluorocarbons, and under conditions of increased pressures or atmospheric pressures. Such steps may be followed by extraction using supercritical conditions known to those skilled in the art, particularly supercritical $CO_2$.

Compositions of the present invention comprise an extract of *Areca catechu* having a ratio of alkaloids that is not found in the naturally-occurring plant or previously made extracts. An embodiment of the compositions of the present invention comprises an extract of *Areca catechu* which is higher in the soluble carboxylic acid alkaloids than in the less soluble ester compounds of the nut. Compositions also comprise pharmaceutical and nutriceutical compositions such as a rapid-dissolving tablet containing extracts of *Areca catechu*.

DETAILED DESCRIPTION OF THE INVENTION

The present invention comprises methods and compositions of *Areca catechu*, particularly the Areca nut. As used herein, "Areca" or "*Areca catechu*" refers to the Areca catechu nut. Methods of the present invention comprise extraction methods to produce extracted Areca compositions, which include both the materials extracted from the Areca and the extracted residue, methods of making Areca compositions such as dietary supplements and nutriceuticals, and methods of providing dietary aids for conditions in humans and animals. Compositions of the present invention comprise compositions resulting from extraction of *Areca catechu*, compositions of extracted *Areca catechu* that have ratios of compounds that are not found in the native plant material or in extracts made prior to the present invention, and compositions for dietary supplements or nutriceuticals that are suitable for administration to humans or animals.

Aspects of the invention provide extracts of *Areca catechu* as a paste, powder, or in other forms, which allows the compounds in the extract, such as alkaloids, to be used in dietary supplements. Because *Areca catechu* paste is not always well suited for processing into consumable form or for distribution, a dry, flowable *Areca catechu* powder is also contemplated by the present invention. Other aspects of compositions of the present invention comprise *Areca catechu* extracts in the form of a rapid-dissolve tablet.

Methods of the present invention comprise extracting the nuts or fruits of the *Areca catechu* palm. One aspect of the methods comprises isolating the alkaloids of the Areca seed so the alkaloids can be incorporated into compositions such as dietary supplements for physical conditions such as stimulatory effects on the central nervous system. Methods of extracting include steps comprising supercritical fluids extraction. Although supercritical $CO_2$ has been used to extract alkaloid components from other plant species, extraction of the Areca seeds by themselves has been unsuccessful to date. Other extraction steps of the present methods include the transformation of the arecoline (an alkaloid methyl ester) into Arecaidine (an alkaloid carboxylic acid), and the transformation of guvacoline (an alkaloid methyl ester) to guvacine (an alkaloid carboxylic acid).

The methods of the present invention can be used to produce extracted compound compositions that have characteristics that are different than the native plant material and other known extracted compositions. For example, an aspect of the compositions made by the methods taught herein include compositions comprising an *Areca catechu* extract having an altered alkaloid ratio. For example, using the methods taught herein, compositions comprising an *Areca catechu* extract having a decreased percentage of arecoline and a decreased percentage of guvacoline, when compared to native plant material, can be made. Other compositions comprise alkaloid ratios between the methyl ester alkaloids and the carboxylic acids that are different from native plant materials or extracts made prior to the present invention. The transformation of the ester components of the extract into the corresponding acid components also increases overall solubility of the extract.

The Areca nut, like many nuts, contains a high level of lipids. These lipids are a complicating factor in the extraction of water-soluble compounds from Areca nuts. The Areca nut comprises approximately 0.2% to 1.7% by weight alkaloid compounds. Of that amount, approximately 40-85% is arecoline, 10 to 40% is Arecaidine and guvacine is 2 to 30%. Other alkaloids present include guvacoline and areaolidine. For example, a measurement of the nut reveals that the total alkaloid content is approximately 1.14% mass of the dried nut, then of that alkaloid content, approximately 26.5% is guvacine, 25.6% is Arecaidine, and 47.9% is arecoline. Other compounds present in the nut include tannins, which are water soluble compounds that comprise about 20%, by weight, of the nut.

One method of extracting the desired alkaloid compounds from the nut comprises a solvent extraction step comprising extracting a dried powder of Areca nut with water at about 10° C. to 80° C., for approximately 15 minutes to approximately 150 minutes, and preferably at least 60 minutes. A pH adjustment step may occur during or after the solvent extracting step to convert the ester alkaloid compounds into carboxylic acid alkaloid compounds. This extraction step yields an extraction product composition comprising alkaloids, tannins and a low amount of lipids. Tannins are removed from this composition by the addition of adsorbents, such as activated charcoal, or by anion exchange resins. After removal of the tannins, a pH adjustment step may occur. A pH adjustment step, used for converting ester compounds into carboxylic acid compounds comprises adjusting the pH to at least a pH of 12, optionally in the presence of a reducing agent, such as ascorbic acid, and at a temperature of 50° C., for a time period of not less than 15 minutes. It is this step that converts the ester compounds into the carboxylic acid compounds, such as arecoline to Arecaidine. The amount of conversion can be determined by measuring the initial content of the ester compounds, such as arecoline, and then adding the amount of base necessary to convert the desired percentage of the ester compounds, arecoline, to the carboxylic compound, Arecaidine. After the conversion, the pH is then lowered to approximately pH 6-8. The conversion of ester compounds to carboxylic compounds is also used to convert guvacoline to guvacine.

According to one embodiment of the present invention, a process for extracting arecoline, Arecaidine, guvacoline and guvacine from the *Areca catechu* seed, also known as the nut, is provided. The *Areca catechu* seed is isolated from the plant, dried, and then ground into a powder. The powder is then dissolved in a solvent and subjected to a supercritical extraction procedure. The pressure and temperature are stabilized from between about 200 bar to about 600 bar and about 20° C. to about 70° C. The resulting extracted material appears as in paste, oil, and/or resin (collectively, "paste") form and is collected. The spent supercritical extractant can either be recycled for future use or vented into the atmosphere. The extractant-to-feed ratio (kg of extractant versus kg of *Areca catechu*) may range from about 5:1 to about 100:1.

The extracted Areca paste is then suspended in water and mixed vigorously for a period between about 10 minutes to about 60 minutes to produce and maintain micron-sized particles. The temperature of the water may be from room temperature to about 70° C. to facilitate efficient mixing and ester cleavage. A suitable chemical base is added to raise the pH of the aqueous solution to a pH of between about 8.0 to about 12.0. The pH of the solution is then held for a period of time between about 15 minutes to about 2.5 hours. The pH of the aqueous solution is then returned to a neutral pH using a suitable acid.

Suitable solvents for dissolving the ground Areca powder include, but are not limited to methanol, ethyl alcohol, or water. In one embodiment of the invention, ethyl alcohol is preferred.

Suitable extractant materials for effecting supercritical extractions included, but are not limited to carbon dioxide, hydrocarbons, hydrofluorocarbons, hydrochlorofluorocarbons, chlorofluorocarbons and other compressible gases. Included among the suitable extractant materials are HFC-23, HFC-32, HFC-125. HFC-134a, HFC-143a, HFC-152a. R-404a, R-407c, R-410a. HCFC-22, HCFC-123, HCFC-141b, HCFC-142b. R-502, R-11, R-12, and R-113. Compressible gases include, but are not limited to propane and butane (and isomers thereof), and ethers. Non-limiting examples of useful ethers include dimethyl ether and diethyl ether. The extractant materials are commercially available.

The extraction step may alternatively be conducted using liquid carbon dioxide, or supercritical phase carbon dioxide in combination with an organic solvent, as defined above, as a modifier.

Suitable chemical bases for raising the pH of the extract solution include, but are not limited to, hydroxy bases such as sodium hydroxide or potassium hydroxide.

Suitable acids for returning the pH of the solution to a neutral pH include, but are not limited to, hydrochloric acid.

In an alternative embodiment of the present invention, the process described above may be simplified and process steps may be eliminated by homogenizing the Areca paste in water in the presence of suspended magnesium carbonate. The addition of magnesium carbonate raises the pH sufficiently to impart the transformation of the ester components into the acid components of the Areca since the magnesium carbonate acts as a weak base and raises the pH above a value of 11.0. An antioxidant, such as, but not limited to ascorbic acid or another suitable antioxidant, may be added to preclude any oxidation of the alkaloid substances.

The amount of magnesium carbonate necessary to raise the value of the pH in the solution ranges from about 250-400 grams of magnesium carbonate per about 250 grams of the Areca powder. The amount of antioxidant necessary to preclude oxidation ranges from about 15-30 grams of antioxidant per about 250 g of Areca powder.

Methods of the present invention comprise supercritical extractions at high pressures between 450 bar and 700 bar, and between 70-100° C., with 10-20% by weight solvent modifier. The solvent modifier may be water, ethanol or ethyl acetate, or a combination of them. The solvent to feed ratio may vary from 10/1 to 20/1. This results in an extracted product that extracts the alkaloids along with a high percentage of lipids. This extraction may be preceded by steps including soaking the feedstock material, the ground dried nut material, in a solution of water and calcium or sodium hydroxide prior to extraction. This soaking at a pH of at least 12 also promotes the transformation of the ester compounds into carboxylic acid compounds.

The resulting extract composition may be used or may be further processed to remove lipids present in the composition. The extraction material is collected and further extracted at a temperature range of 40-60° C., and a pressure range of 300 to 350 bar to extract the lipids. Another method of removal of lipids comprises washing the extract with a water, ethanol or ethyl acetate solution or a combination of them, and then spray drying or freeze drying the resulting extract to obtain purified alkaloid crystals.

Another method of the present invention comprises extracting the dried nut powder with organic or aqueous solutions or combinations, such as ethanol, water or ethyl acetate or combinations. This extract product composition contains alkaloids, tannins and a low amount of lipids. This extract can be used as is or can be further extracted using supercritical conditions. Either the first solvent extraction or the supercritical extraction may also comprise the addition of a solution of water that is 15% sodium or calcium hydroxide, as a base solution with a pH of at least 12. This solution is applied to the powdered nut or to the extract in a range of 15-20% by weight prior to the first extraction step or the supercritical extraction step. This basic solution promotes the transformation of the ester compounds into the carboxylic acid compounds. The lipids and waxes that may be present in the extraction products may be removed by extracting with supercritical carbon dioxide at pressures between 300-350 bar and 40-60° C. The extraction products may be used in the formulations taught below.

Compositions of the present invention comprise compositions resulting from the extraction of *Areca catechu* nut. These compositions include both the extract product resulting from extractions methods and the residue from the extraction, including plant material that was extracted and intermediary extracted residues from subsequent extractions. Extract product compositions comprise extracted products that have an altered alkaloid profile that is different from the native plant material. An aspect of compositions of the present invention comprises compositions that have an alkaloid profile that has more carboxylic acid alkaloids than ester alkaloids. For example, compositions of the present invention comprise extracts of Areca nut that have a higher percentage of Arecaidine than arecoline, and compositions that comprise a higher percentage of guvacine than guvacoline. Compositions of the present invention also comprise alkaloids, tannins and a small amount of lipids. Such compositions may or may not comprise alkaloids wherein the carboxy alkaloids are found in a higher percentage than ester alkaloid compounds. Compositions of the present invention also comprise the residue of extracted Areca nut from which at least one compound has been removed, such as tannins, alkaloids or some lipids.

Compositions of the present invention comprise extracted product compositions wherein the arecoline content is from approximately 0 to approximately 99% of the Arecaidine content. Compositions also comprise extracted product compositions wherein the ester alkaloid content is from approximately 0 to approximately 99% of the carboxy acid alkaloid content. Compositions of the present invention also comprise extracted product compositions wherein the guvacoline content is from approximately 0 to approximately 99% of guvacine content.

Compositions of the present invention comprise extraction product compositions comprising alkaloid compounds. Such alkaloids include, but are not limited to, arecoline, Arecaidine, areaolidine, guvacine, guvacoline. Compositions also comprise other compounds, including but not limited to caffeine, theobromine and theophylline, and herbs or extractions of herbs or other plant materials such as extracts of kava, chocolate, sage, guarana, muira puama, and maca.

Compositions of the present invention having a higher percentage of carboxy acid alkaloids can be derived from extracted alkaloid compositions by adding a step in the extraction methods of raising the pH of the solution. By raising the pH of the Areca extract solution, the ester form of the alkaloids (arecoline, and guvacoline) is converted quantitatively into the carboxylic acid form of the alkaloids (Arecaidine and guvacine). That is, for example, the arecoline is converted to Arecaidine. One of ordinary skill in the art would understand that the pH step can be controlled quantitatively so as to convert exact amounts of an ester component into exact amounts of the corresponding acid component, thus changing the natural ratios of the alkaloids into new ratios that define novel materials. For example, the resulting *Areca catechu* product may have an alkaloid concentration ratio converting 100% of the arecoline into Arecaidine.

The value of the alkaloid make-up for a sample of a processed *Areca catechu* product can be determined using conventional analytical techniques, such as high performance liquid chromatography and/or gas chromatography or any other technique known to one of ordinary skill in the art.

Compositions of the present invention comprise extracted *Areca catechu* nut compositions that are different from the native *Areca catechu* nut. As used herein, Areca catechu nut means *Areca catechu* nut that has not been extracted by any solvents or other processes that would alter the chemical nature of the nut, other than picking the nut and drying it. For example, the present invention comprises a composition, comprising an extract of *Areca catechu* nut wherein the alkaloid profile is different from that of native *Areca catechu* nut. The present invention further comprises compositions wherein the amount of carboxy acid alkaloid compounds is greater than the amount of ester alkaloid compounds, compositions wherein the amount of ester alkaloid compounds is less than that of native *Areca catechu* nut, compositions wherein the amount of arecoline is less than the amount of Arecaidine, compositions wherein the amount of guvacoline is less than the amount of guvacine, compositions wherein the amount of arecoline and guvacoline is less than the amount of Arecaidine and guvacine.

The present invention comprises compositions comprising an extract of Areca catechu, comprising arecoline, Arecaidine, guvacoline and guvacine in concentrations that are different from those concentrations found in native *Areca catechu* nut, extracts wherein the amounts of arecoline and guvacoline are less than the amounts of Arecaidine and guvacine. The present invention comprises *Areca catechu* compositions, comprising an alkaloid profile comprising an arecoline component, an Arecaidine component, a guvacoline component, a guvacine component, wherein the alkaloid profile has a ratio of the Arecaidine component to the arecoline component by weight of greater than about 1.0. The present invention also comprises ingestible products that comprise the *Areca catechu* compositions taught herein. For example, the present invention comprises compositions comprising a rapid dissolve tablet, comprising an *Areca catechu* extract having an alkaloid profile wherein the carboxy acid alkaloid compounds are in a higher concentration than the ester alkaloid compounds.

In another embodiment of the present invention, a novel *Areca catechu* product is provided. The novel product, produced by the processes described herein, is made up of different ratios of the four alkaloids of Areca, arecoline, Arecaidine, guvacoline and guvacine. By varying the pH step in the processes described above, *Areca catechu* products having 0% arecoline and 100% Arecaidine can be achieved. Similarly, Areca catechu products having ratios of 99:1 Arecaidine to arecoline or guvacine to guvacoline, 98:2, 97:3, 96:4, and so on, may be obtained.

The present invention comprises compositions and methods of making such compositions. The methods comprise making and using compositions, but not limited to, compositions described herein comprising an extract of *Areca catechu* nut wherein the alkaloid profile is different from that of native *Areca catechu* nut, compositions wherein the amount of carboxy acid alkaloid compounds is greater than the amount of ester alkaloid compounds, compositions wherein the amount of ester alkaloid compounds is less than that of native *Areca catechu* nut, compositions wherein the amount of arecoline is less than the amount of Arecaidine, compositions wherein the amount of guvacoline is less than the amount of guvacine, and compositions wherein the amount of arecoline and guvacoline is less than the amount of Arecaidine and guvacine.

Methods of making and using compositions of the present invention comprise making and using extracts of *Areca catechu*, comprising arecoline, Arecaidine, guvacoline and guvacine in concentrations that are different from those concentrations found in native *Areca catechu* nut, extracts wherein the amounts of arecoline and guvacoline are less than the amounts of Arecaidine and guvacine, and compositions comprising an alkaloid profile comprising an arecoline component, an Arecaidine component, a guvacoline component, a guvacine component, wherein the alkaloid profile has a ratio of the Arecaidine component to the arecoline component by weight of greater than about 1.0.

The present invention comprises compositions and methods for making and using such compositions, where the compositions comprise oral delivery dosage formulations of the extracts and Areca nut compositions taught herein. An aspect of the present invention comprises a rapid dissolve tablet, comprising an *Areca catechu* extract having an alkaloid profile wherein the carboxy acid alkoid compounds are in a higher concentration than the ester alkaloid compounds. Methods for making the compositions taught herein comprise extracting an *Areca catechu* nut powder with a first solution that results in a first extraction product containing at least the alkaloid compounds, and extracting the first extraction product under supercritical conditions. An aspect of the methods comprises a first solution of water, alcohol, or water and alcohol mixture. An aspect of the methods comprises supercritical conditions comprising extracting under supercritical $CO_2$ conditions. An aspect of the methods comprises a pH adjustment step that occurs after extraction by the first solution or before extraction by the first solution. An aspect of the present invention comprises methods of making an *Areca catechu* extract, comprising, extracting a dried *Areca catechu* nut powder having a plurality of alkaloids in a first distribution profile of ester and carboxy acid alkaloid compounds with a first solvent in which the alkaloids are soluble to form an extract; removing tannins from the extract, and altering the alkaloid distribution of ester and carboxy acid alkaloid compounds to result in a second distribution profile. An aspect of the methods comprises altering the alkaloid distribution steps comprising adding a solution that raises the pH of the resulting solution to at least 12. An aspect of the methods comprises adding the solution that increases the pH of the resulting solution to the first solution, after the tannins are removed, prior to the step wherein the tannins are removed, or at one or more of these steps. The methods of making and using the compositions of the present invention comprise compositions wherein the second distribution profile has less ester alkaloid compounds than did the first alkaloid distribution profile, compositions wherein the second distribution profile has a higher amount of Arecaidine than arecoline, and compositions wherein the second distribution profile has a higher amount of guvacine than guvacoline.

A method of the present invention comprises extraction of the ground Areca nut. The method comprises using water at a temperature of between approximately 0° C. and approximately 60° C., more preferably between approximately 5° C. and 25° C., or temperatures that preclude the extraction of fats, to ground Areca nut, preferably dried ground Areca nut. Temperatures at 35° C. and lower release few to no fats from the nut into the extraction solution. The ratio of water to dried Areca nut may be different depending on whether the extraction is under pressure or at atmospheric pressure. For example, under pressure extractions, between 50 psi and 1500 psi, or between 700 psi and 1300 psi, bed volume washes of water may be from approximately 3 to 5 bed volumes. The bed volumes relate to the bulk density of the ground Areca nut. For example, if the bulk density is around 0.5, a generally found amount for ground Areca nut, then 5 kg of ground Areca nut will generally require about 10 liters of water for extraction. The residence time for contact of the water with the ground Areca nut is at least 30 minutes. The residence time can be 150 minutes, and times of 30 minutes to 1 hour are generally used. In this example, with 0.5 bulk density, there would be three bed washes of 10 liters each, for a total of 30 liters for the three different washes with residence times as indicated for the exposure of the ground Areca nut to the water. For extractions at atmospheric pressure, the water volumes, as in number of washes, is increased from pressurized conditions. For example, the solvent or water to ground Areca nut powder is approximately 10 to 1.

The pH of the water is between pH 3 to pH 6, or neutral or slightly acidic. The solution can be pressurized or not, preferably the solution is pressurized above atmospheric pressure. After sufficient residence time, the resulting extract is collected by filtration or other means, such as settling or centrifugation, to remove the solid material. The liquid extract is then added to an anion exchange resin, such as, but not limited to, Purolite brand A850 resin, or to activated charcoal. The amount of anion exchange resin or charcoal used is not critical, but suggested amounts are 1 gram of resin/charcoal for between 0.05 g to 0.25 g of solid starting material. The solids content measurement is used to determine the amount of resin needed. For example, solids content can be determined by differential mass determination. Instruments for measuring solids content are known. In general, a sample of the extraction liquid is placed in a small tray, the weight is measured, and the tray is heated to evaporate the water. The residue and tray are reweighed and from the difference, in mass, of the first and second weights, the percentage of solids of the liquid is calculated. In general, this number is low, for example, between 0.01 and about 10, generally about 4.0. These solids comprise water soluble (if water is the solvent) compounds, among others, the tannins and the alkaloid compounds.

Once the solids content is determined by any variety of means, the anion exchange resin or activated charcoal is added to the solution. The amount of resin or charcoal needed is at the least (by mass) 20 to 40 times the mass of the solids content that was determined. For example, in the 30 liters of a pressurized water extraction of ground Areca nut, if the solids content of the liquid extract is 4%, then 1.2 kg of solids were extracted from the ground Areca nut. To the 30 liters of liquid extract, are added 24 to 48 kg of anion exchange resin. This can be done in batch processing steps, or by using a container for the anion exchange resin or activated charcoal and passing the liquid extract through the resin or charcoal, such as is used in chromatography methods. Water then used to wash the resins to remove the alkaloid compounds from the resin or charcoal. Generally there is a large volume of water used to Wash the resin or charcoal, and the liquid is then removed through various means such as vacuum distillation, and taken to dryness by known methods such as freeze drying, spray drying or refractive window drying. A preferred method is freeze drying.

Prior to adding the resin or charcoal, the pH of the liquid extract is adjusted to approximately a pH of 12. Use of a strong base, such as NaOH, will adjust the pH to approximately 12. The temperature of the solution is also adjusted to about 50° C. to 60° C., preferably at 50° C. and is held at that temperature and pH, preferably for approximately 15 minutes to 1 hour. The increase in temperature aids in the conversion of the ester alkaloid to the carboxy acid alkaloid. For example, the liquid extract can transit through the resin bed at a temperature of 50° C. for about 15-60 minutes, with the pH of the liquid extract at about 12. Generally, in about 30 minutes of time in these conditions, sufficient amounts of carboxy acid alkaloid compounds can be obtained. The solution is allowed to be contact with the resin for a period of time to allow the anion exchange resin to remove the chromophoric substances and tannins from the solution. This period of time can range from minutes to hours. Once the solution clears, then the liquid is collected and the pH is adjusted to approximately neutral, with an acidic solution such as HCl. The solution can then be processed by methods taught herein, such as freeze-drying the solution. The resulting dried material, having an altered alkaloid profile from the native material, can then be processed by the methods taught herein to be used in products such as dietary supplements and nutriceuticals.

In another embodiment of the present invention, a process for forming the novel *Areca catechu* extract product having an alkaloid distribution that is particularly well suited for delivery to human subjects, e.g., via a rapidly-dissolving tablet, is provided. The extracted product compositions taught herein can be administered to humans or animals in pharmaceutical preparations known to those skilled in the art.

One form of the products of the present invention is incorporation of the extracted product compositions into a rapidly dissolving formulation, such as that taught by inventions such as are found in U.S. Pat. No. 5,298,261 to Pebley, et al., which is herein incorporated in its entirety. In general, such a rapidly disintegrating tablet is a tablet that rapidly disintegrates in aqueous solution and includes a partially collapsed matrix network that has been vacuum-dried above the collapse temperature of the matrix. The matrix is preferably at least partially dried below the equilibrium freezing point of the matrix. Vacuum drying the tablet above its collapse temperature instead of freeze drying it below its collapse temperature provides a process for producing tablets with enhanced structural integrity, while rapidly disintegrating in normal amounts of saliva. The tablet preferably comprises the active agents and compositions taught herein. The matrix network of the tablet preferably includes a gum, a carbohydrate and the extracted product composition. Especially preferred embodiments also include a flavoring, a sweetener and surfactant. The gum is preferably acacia, guar, xanthan, carrageenan or tragacanth gum. The carbohydrate is preferably mannitol, dextrose, sucrose, lactose, maltose, maltodextrin or corn syrup solids In methods of the present invention, such methods including a process for making a rapidly-dissolving tablet, the extract paste obtained after supercritical extraction or a dried extract product composition is mixed with a suitable solvent, as defined above, along with a suitable food-grade carrier material. The mixture is spray air-dried using techniques known to one of ordinary skill in the art to produce a powder having grains of very small *Areca catechu* extract particles combined with the food-grade carrier material.

Suitable food-grade carrier materials include, but are not limited to, maltodextrin, dextrose, whey protein, carboxymethylcellulose, or starch.

In an alternative process, an emulsion of *Areca catechu* paste or a dried extract product composition is formed in water or ethyl alcohol using, e.g., magnesium carbonate, magnesium carbonate with silica (at up to about 2% by weight), or a food-grade carrier as defined above. The emulsion is then dried and powdered.

In another alternative process, the extract is processed with supercritical carbon dioxide and a food-grade carrier, as defined above, and is then subjected to a rapid decompression of the supercritical fluid. As the fluid evaporates, the extract and Areca catechu are deposited as micron-sized particles. For direct ingestion, for example, a paste can be sweetened and flavored by any means known in the art. In addition or alternatively, the paste can be mixed with other dietary supplements, flavors, anti-oxidants, and/or other botanical extracts.

The resulting powder from any of the processes described above can be formed into a tablet that, when placed in the mouth, dissolves rapidly over a period of between about 5 seconds to about 120 seconds and preferably in about 15 to about 60 seconds. A tableting powder can be formed by combining between about 18% to about 60% by weight of the powdered *Areca catechu* extract composition with between about 30% to about 80% by weight of a dry water-dispersible adsorbant such as, but not limited to, magnesium carbonate, or a diluent, such as, but not limited to lactose. Other dry tablet additives, such as, but not limited to, one or more of a sweetener, flavoring and/or coloring agents, a binder, such as acacia or gum arabic, a lubricant, a disintegrant, and a buffer, can also be added to the tableting powder. The dry ingredients are screened to a particle size of between about 50 to about 150 mesh. Preferably, the dry ingredients are screened to a particle size of between about 80 to about 100 mesh.

A wide variety of tablet formulations can be made. Preferably, the tablet has a formulation that results in a rapid dissolution or disintegration in the oral cavity. The tablet is preferably of a homogeneous composition that dissolves or disintegrates rapidly in the oral cavity to release the *Areca catechu* extract content over a period of between about 5 seconds to about 120 seconds or more, preferably between about 15 to about 60 seconds.

Various rapid-dissolve tablet formulations known in the art can be used. Representative formulations are disclosed in U.S. Pat. Nos. 5,464,632, 6,106,861, and 6,221,392, the entire contents of which are expressly incorporated by reference herein. A particularly preferred tableting composition or powder contains about 10% to about 60% by weight of the *Areca catechu* extract powder and about 30% to about 60% of a water-soluble diluent. Suitable diluents include, but are not limited to, lactose, dextrose, sucrose, mannitol, and other similar compositions. Lactose is a preferred diluent, but mannitol adds a pleasant, cooling sensation and additional sweetness in the mouth. More than one diluent can be used. A sweetener can also be included, preferably in an amount of between about 3% to about 40% by weight depending on the desired sweetness.

Preferred sweetening substances include, but are not limited to, sugar, saccharin, sodium cyclamate, aspartame, and Stevia extract, used alone or in combination. Flavorings, such as but not limited to, mint, cinnamon, citrus (e.g. lemon or orange), can also be included, preferably in an amount between about 0.001% to about 4% by weight.

Typically, this tableting composition will maintain its form without the use of a binder. However, if needed, various binders are suitable and can be added in an amount of between about 5% to about 15% or as necessary. Any binder known to one of ordinary skill in the art may be used. Preferred binders include, but are not limited to, acacia or gum arabic. Alternative binders include sodium alginate, extract of Irish moss, panwar gum, ghatti gum, mucilage of isapol husks, carboxymethylcellulose. hydroxyethylcellulose, methylcellulose, polyvinylpyrrolidone, VEEGUM® (available from R.T Vanderbilt Co., Inc. of Norwalk. Conn.), larch arabogalactan, gelatin, Kappa carrageenan, copolymers of maleic anhydride with ethylene or vinyl methyl ether.

A tablet according to this aspect of this invention typically does not require a lubricant to improve the flow of the powder for tablet manufacturing. However, if it is so desired, a lubricant may be provided. Any lubricant known to one of ordinary skill in the art may be used. Preferred lubricants include, but are not limited to, talc, magnesium stearate, calcium stearate, stearic acid, hydrogenated vegetable oils, and carbowax in amounts of between about 2% to about 10% by weight.

Similarly, a disintegrant is not expected to be necessary to produce rapid dissolve tablets using the present tablet composition. However, a disintegrant can be included to increase the speed with which a resulting tablet dissolves in the mouth. If desired, between about 0.5% to about 1% by weight of a disintegrant can be added. Any disintegrant known to one of ordinary skill in the art may be used. Preferred disintegrants include starches, clays, celluloses, algins, gums, crosslinked polymers (including croscarmelose, crospovidone and sodium starch glycolate), VEEGUM® HV, agar, bentonite, natural sponge, cation exchange resins, aliginic acid, guar gum, citrus pulp, sodium lauryl sulphate.

It is also generally considered unnecessary to buffer the tablet composition. However, a buffer may be beneficial in specific formulations. Any buffering agent known to one of ordinary skill in the art may be used. Preferred buffering agents include, but are not limited to, mono- and di-sodium phosphates and borates, basic magnesium carbonate and combinations of magnesium and aluminum hydroxide.

In one embodiment, the tableting powder is made by mixing in a dry powdered form the various components as described above. e.g., active ingredient (*Areca catechu* extract), diluent, sweetening additive, and flavoring. etc. An additional 10% to about 15% of the active extract of the active ingredient can be added to compensate for losses during subsequent tablet processing. The mixture is then sifted through a sieve with a mesh size preferably in the range of about 80 mesh to about 100 mesh to ensure a generally uniform composition of particles. The total weight of the *Areca catechu* extract in the form of a dry flowable powder in a single oral dosage is typically in the range of about 80 mg to about 600 mg.

The tablet can be of any desired size, shape, weight, or consistency. An important consideration is that the tablet is intended to dissolve in the mouth and should therefore not be of a shape that encourages the tablet to be swallowed. The larger the tablet, the less it is likely to be accidentally swallowed, but the longer it will take to dissolve or disintegrate. In a preferred form, the tablet is a disk or wafer of about ⅛ inch to about ¾ inch in diameter and about 0.2 inch to 0.08 inch in thickness, and has a weight of between about 160 mg to about 1,200 mg. In addition to disk, wafer or coin shapes, the tablet can be in the form of a cylinder, sphere, cube, or other shapes. Although the tablet is preferably homogeneous, the tablet may alternatively be comprised of regions of powdered *Areca catechu* extract composition separated by non-*Areca catechu* extract regions in periodic or non-periodic sequences, which can give the tablet a speckled appearance with different colors or shades of colors associated with the *Areca catechu* extract regions and the non *Areca catechu* extract regions.

The pharmaceutical or nutriceutical compositions of the present invention are administered to humans or animals to achieve a desired physiological reaction. A preferred method of administration comprises administering an effective amount of an extracted product composition taught herein in an acceptable pharmaceutical carrier. One method of administering compositions taught herein comprises replacement of the chewed betel quid with compositions taught herein. For example, an oral dosage form of the extracted Areca carboxy acid alkaloid compounds are administered one or more times a day to achieve the effective level of physiological response.

The foregoing description includes the best presently contemplated mode of carrying out the invention. This description is made for the purpose of illustrating the general principles of the inventions and should not be taken in a limiting sense. This invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention.

All terms used herein are considered to be interpreted in their normally acceptable usage by those skilled in the art. Patents and patent applications or references cited herein are all incorporated by reference in their entireties.

EXAMPLES

Example 1

A formulation of the present invention comprises the following:

| Component | Percent |
|---|---|
| Extract of *Areca Catechu* | 20.7 |
| Extract of *Piper Betel* | 1.8 |
| Stevioside (Extract of *Stevia*) | 15.2 |
| Theobromine | 20.6 |
| Caffeine | 6.2 |
| Theophylline | 0.4 |
| Vitamin C | 1.9 |
| Magnesium Carbonate | 33.2 |
| TOTAL | 100.0 |

Extract of Areca Catechu containing ratio of Arecaidine component to arecoline component by weight of greater than about 1.0.

The formulation can be made into any oral dosage form and administered once a day to persons or animals. For those accustomed to taking Areca, more frequent administration may be needed. Optionally, the amount of Areca extract can be increased in each individual dosage form, and taken as needed to maintain the level of effectiveness.

REFERENCES

1. Spinella, Marcello. The Psychopharmacology of Herbal Medicine; Plant Drugs that Alter Mind, Brain, and Behavior, MIT Press, 2001, ISBN 0-262-69265-1.

What is claimed is:

1. An *Areca catechu* extract composition, comprising, an effective amount of an *Areca catechu* nut extract having an altered alkaloid profile comprising Arecaidine and arecoline, wherein the concentration of Arecaidine is greater than the concentration of arecoline therein; and wherein the composition is substantially tannin-free.

2. The composition of claim 1, wherein in the altered alkaloid profile of the extract, an amount of carboxy acid alkaloid compounds is greater than an amount of ester alkaloid compounds therein.

3. The composition of claim 2, wherein the amount of ester alkaloid compounds is less than that of native *Areca catechu* nut.

4. The composition of claim 1, wherein the extract further has an altered alkaloid profile comprising guvacoline and guvacine, wherein the amount of guvacoline is less than the amount of guvacine therein.

5. The composition of claim 4, wherein in the altered alkaloid profile of the extract, the amount of arecoline and guvacohine is less than the amount of Arecaidine and guvacine therein.

6. An extract of *Areca catechu*, comprising arecoline, Arecaidine, guvacoline and guvacine in concentrations that are different from those concentrations found in native *Areca catechu* nut and wherein the extract is substantially tannin-free.

7. The extract of claim 6, wherein the amounts of arecoline and guvacoline are less than the amounts of Arecaidine and guvacine.

8. An *Areca catechu* extract composition, comprising an alkaloid profile comprising an arecoline component, an Arecaidine component, a guvacoline component, a guvacine component, wherein the alkaloid profile has a ratio of the Arecaidine component to the arecoline component by weight of greater than about 1.0, and wherein the composition is substantially tannin-free.

9. A rapid dissolve tablet, comprising an *Areca catechu* extract having an altered alkaloid profile comprising carboxy acid alkaloid compounds and ester alkaloid compounds, wherein the carboxy acid alkaloid compounds are in a higher concentration than the ester alkaloid compounds therein, and wherein the extract is substantially tannin-free.

* * * * *